(12) United States Patent
Isozaki et al.

(10) Patent No.: US 7,193,078 B2
(45) Date of Patent: Mar. 20, 2007

(54) PROCESS FOR PRODUCTION OF O-ALKYLATED RAPAMYCIN DERIVATIVES

(75) Inventors: Masashi Isozaki, Kanagawa (JP); Tetsuro Kawanishi, Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 51 days.

(21) Appl. No.: 11/067,718

(22) Filed: Mar. 1, 2005

(65) Prior Publication Data
US 2005/0192311 A1 Sep. 1, 2005

(30) Foreign Application Priority Data
Mar. 1, 2004 (JP) ............................. 2004-056233

(51) Int. Cl.
*C07D 498/18* (2006.01)
(52) U.S. Cl. .................................... 540/456
(58) Field of Classification Search ................ 540/456
See application file for complete search history.

(56) References Cited

U.S. PATENT DOCUMENTS

2005/0101624 A1  5/2005  Betts et al.
2005/0131008 A1  6/2005  Betts et al.

FOREIGN PATENT DOCUMENTS

WO        94/09010       4/1994

OTHER PUBLICATIONS

L.A. Sorbera et al., "Drug of the Future", SDZ-RAD, Jan. 24, 1999, pp. 22-29, Prous Science, P.O. Box 540, 08080 Barcelona, Spain.
European Search Report.
Moenius, TH et al.: "Tritium Labelling of RAD001-A New Rapamycin Derivative", Journal of Labelled Compounds and Radiopharmaceuticals, 43, pp. 113-120, 2000.
Moenius, TH et al.: "C-14 Labelling of NVP RAD001-A New Rapamycin Derivative", Journal of Labelled Compounds and Radiopharmaceuticals, 42, pp. 29-41, 1999.

*Primary Examiner*—Bruck Kifle
(74) *Attorney, Agent, or Firm*—Buchanan Ingersoll & Rooney PC

(57) ABSTRACT

Disclosed herein is a process for production of an O-alkylrapamycin derivative represented by the general formula (1) below by reaction between rapamycin and alkyl triflate in an organic solvent, characterized in that the reaction is carried out in the presence of trialkylamine.

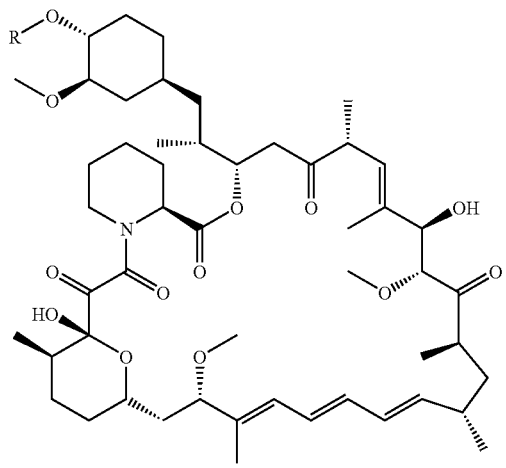

Formula 1

(where R denotes alkyl, arylalkyl, hydroxyalkyl, alkoxyalkyl, acyloxyalkyl, aminoalkyl, alkylaminoalkyl, alkoxycarbonylaminoalkyl, acylaminoalkyl, or aryl.)

This process is capable of producing O-alkylrapamycin derivative efficiently owing to improvement in reaction yields for O-alkylation.

13 Claims, 1 Drawing Sheet

PROCESS FOR PRODUCTION OF O-ALKYLATED RAPAMYCIN DERIVATIVES

BACKGROUND OF THE INVENTION

The present invention relates to a process for producing O-alkylrapamycin derivatives by reaction between rapamycin and alkyl triflate.

Rapamycin is one of macrolide antibiotics produced by *Streptomyces hygroscopicus*. It exhibits immunosuppresive actions, carcinostatic actions, and antifungal actions. Because of such useful pharmaceutical activity, much has been reported about rapamycin derivatives (See Drugs of Future, 1999, 24(1): 22–29).

On the other hand, synthesis of rapamycin derivatives has been reported by Cottens et al (See WO94/09010 official gazette). This document discloses a process for producing an O-alkylrapamycin derivative by reaction between rapamycin and alkyl triflate in the presence of lutidine in toluene (as a solvent). However, it mentions nothing about the yield that is attained by the disclosed process. Further investigation by the present inventors revealed that the yield is only 23% (refer to Comparative Example 1 mentioned later), which suggests that the O-alkylating reaction does not proceed smoothly as desired. Therefore, a great improvement in the process of synthesis has been required for effective use of very expensive rapamycin.

SUMMARY OF THE INVENTION

It is an object of the present invention to provide a process for efficient production of an O-alkylrapamycin derivative. This process is designed to improve yields in the step of O-alkylating. The present invention is based on the idea that increasing the reactivity is a key to the synthesis of rapamycin derivatives mentioned above.

In order to tackle the problem, the present inventors carried out extensive studies, which led to the finding that it is possible to efficiently produce O-alkylrapamycin derivatives in greatly improved yields if the reaction between rapamycin and alkyl triflate is accomplished in the presence of trialkylamine in an organic solvent. The present invention is based on this finding.

The present invention is directed to a process for efficient production of an O-alkylrapamycin derivative, the process being defined in the following paragraphs (1) to (14).

(1) A process for production of an O-alkylrapamycin derivative represented by the general formula (1) below by reaction between rapamycin and alkyl triflate in an organic solvent, characterized in that the reaction is carried out in the presence of trialkylamine;

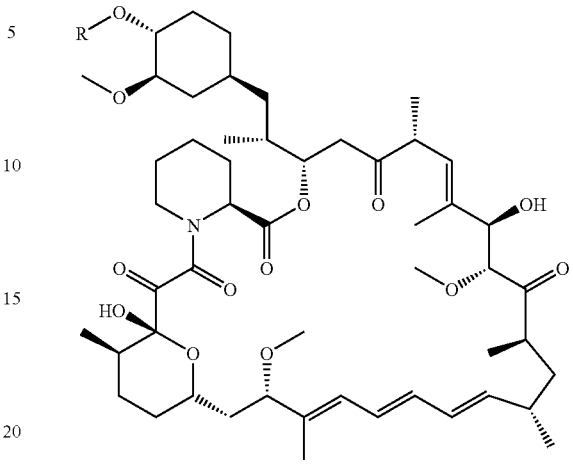

Formula 1 where R denotes alkyl, arylalkyl, hydroxyalkyl, alkoxyalkyl, acyloxyalkyl, aminoalkyl, alkylaminoalkyl, alkoxycarbonylaminoalkyl, acylaminoalkyl, or aryl.

(2) The process for production of an O-alkylrapamycin derivative as defined in (1), wherein the trialkylamine is used in an amount not less than 30 mol per mol of rapamycin.

(3) The process for production of an O-alkylrapamycin derivative as defined in (1) or (2), wherein the trialkylamine is N,N-diisopropylethylamine.

(4) The process for production of an O-alkylrapamycin derivative as defined in any of (1) to (3), wherein the organic solvent is a chlorine-containing organic solvent.

(5) The process for production of an O-alkylrapamycin derivative as defined in (4), wherein the chlorine-containing organic solvent is methylene chloride or chloroform.

(6) The process for production of an O-alkylrapamycin derivative as defined in any of (1) to (5), wherein the organic solvent is used in an amount of 2 to 6 parts by weight for 1 part by weight of rapamycin.

(7) The process for production of an O-alkylrapamycin derivative as defined in any of (1) to (6), wherein the alkyl triflate is used in an amount of 5 to 20 mol per mol of the O-alkylrapamycin derivative.

(8) The process for production of an O-alkylrapamycin derivative as defined in any of (1) to (7), wherein the alkyl triflate is 2-ethoxyethyl triflate.

(9) The process for production of an O-alkylrapamycin derivative as defined in any of (1) to (8), wherein the process includes an additional step for purification in which the O-alkylrapamycin derivative synthesized by the process defined in any of (1) to (8) is placed in a mixed solvent composed of water and at least one water-miscible solvent or placed in water or a water-containing mixed solvent after dissolution in at least one water-miscible solvent, and subsequently allowed to precipitate out.

(10) The process for production of an O-alkylrapamycin derivative as defined in (9), wherein the water-miscible solvent is used in an amount of 2 to 10 parts by weight for 1 part by weight of the O-alkylrapamycin derivative.

(11) The process for production of an O-alkylrapamycin derivative as defined in (9) or (10), wherein the water is used in an amount not less than 10 parts by weight for 1 part by weight of the O-alkylrapamycin derivative.

(12) The process for production of an O-alkylrapamycin derivative as defined in any of (9) to (11), wherein the water-miscible solvent is an alcohol.

(13) The process for production of an O-alkylrapamycin derivative as defined in (12), wherein the alcohol is methanol.

(14) The process for production of an O-alkylrapamycin derivative as defined in any of (9) to (13), wherein the step of precipitation is carried out such that the O-alkylrapamycin derivative is dissolved in a solvent containing at least one water-miscible solvent and subsequently the resulting solution is placed in water or a mixed solvent composed of water and at least one water-miscible solvent.

With the above-mentioned production process according to the present invention, it is possible to improve yields in reaction for O-alkylation and to efficiently produce an O-alkylrapamycin derivative.

DETAILED DESCRIPTION OF THE PREFERRED EMBODIMENTS

Figure 1:
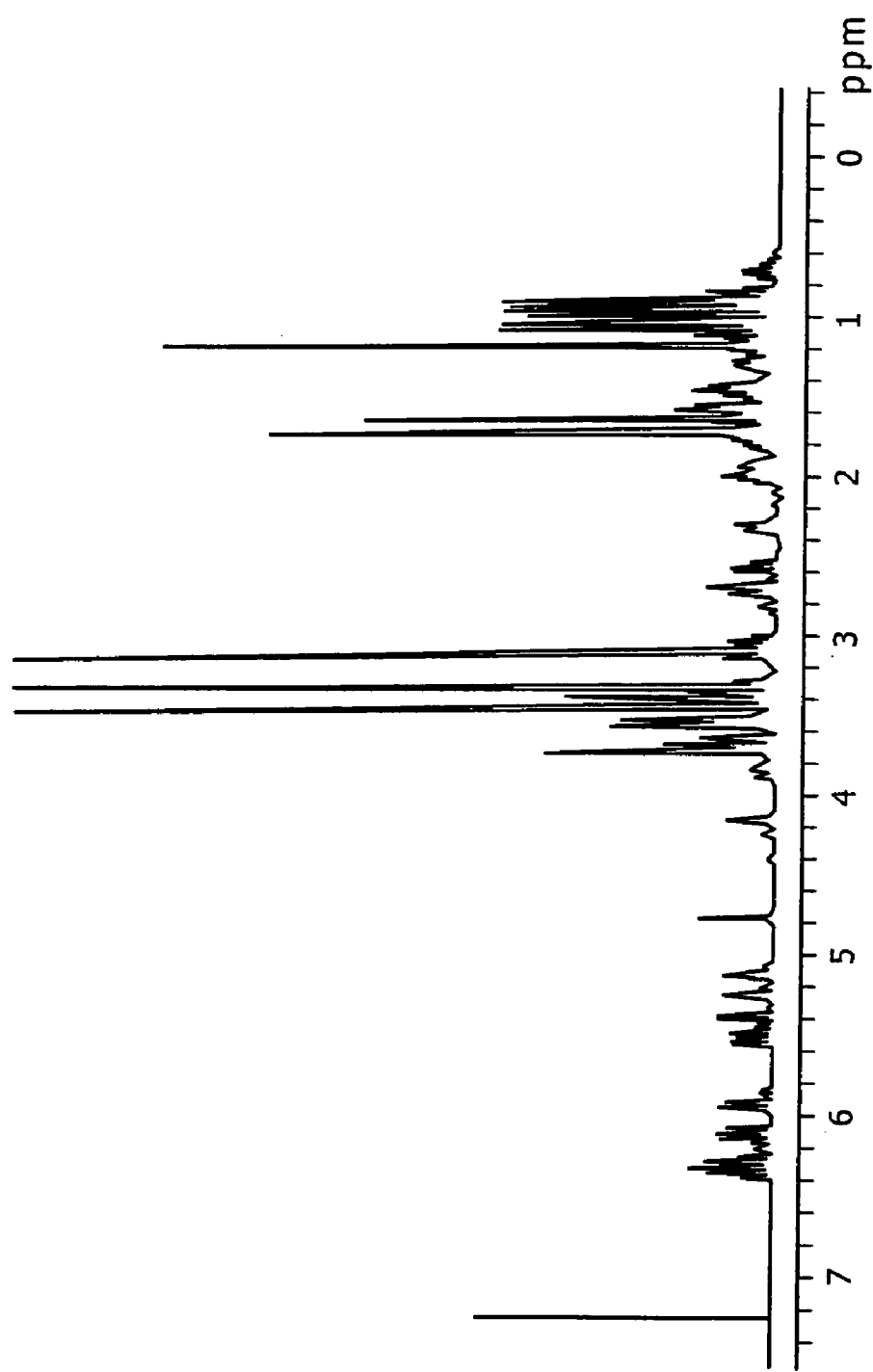
FIG. 1 is an NMR chart which proves that the compound synthesized by the process according to the present invention is O-(2-ethoxyethyl)-rapamycin.

The present invention will be described in more detail in the following.

The present invention covers a process for production of an O-alkylrapamycin derivative represented by the general formula (1) below by reaction between rapamycin and alkyl triflate in an organic solvent, characterized in that the reaction is carried out in the presence of trialkylamine.

Formula 1

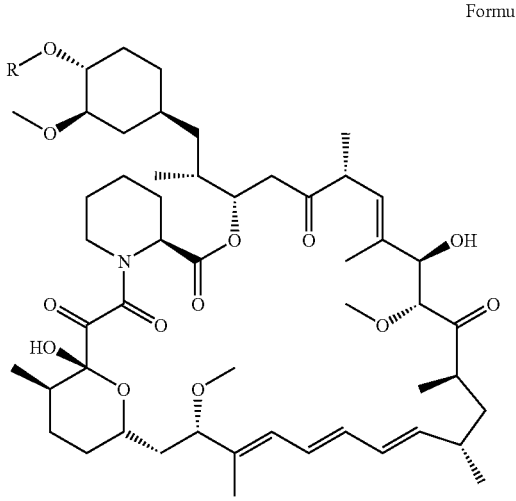

(where R denotes alkyl, arylalkyl, hydroxyalkyl, alkoxyalkyl, acyloxyalkyl, aminoalkyl, alkylaminoalkyl, alkoxycarbonylaminoalkyl, acylaminoalkyl, or aryl.)

An example of the O-alkylrapamycin derivative (with R=alkoxyalkyl) represented by the general formula 1 above is O-(2-ethoxyethyl)-rapamycin represented by the general formula 2 below.

The O-(2-ethoxyethyl)-rapamycin can be produced by reaction between rapamycin and 2-ethoxyethyl triflate in the presence of N,N-diisopropylethylamine in methylene chloride.

Formula 2

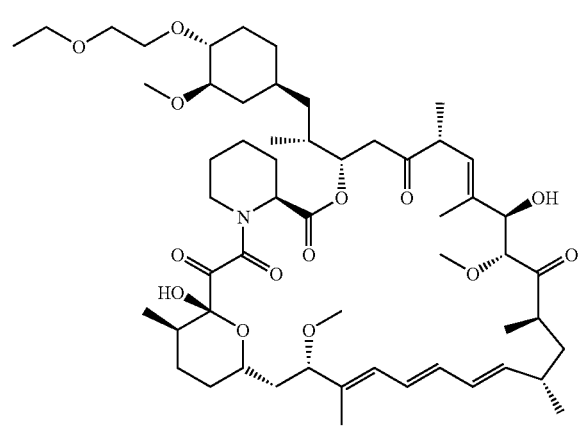

An example of the O-alkylrapamycin derivative (with R=hydroxyalkyl) is O-(2-hydroxyethyl)-rapamycin represented by the general formula 3 below.

The O-(2-hydroxyethyl)-rapamycin can be produced by reaction between rapamycin and t-butyldimethylsilyloxyethyl triflate in the presence of N,N-diisopropylethylamine in methylene chloride, followed by deprotecting of t-butyldimethylsilyl group.

Formula 3

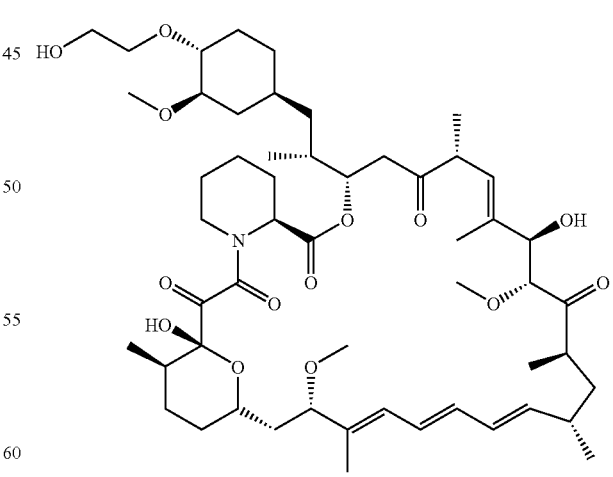

The following are the examples of the trialkylamine which is used in synthesis of O-alkylrapamycin derivatives by the process according to the present invention: trimethylamine; triethylamine; tri-n-propylamine; triisopropylamine; tri-n-butylamine; tri(2-methyl-n-propyl)amine; tri(3-methyl-n-propyl)amine; N,N-dimethylethylamine; N,N-diethylmethylamine; N,N-di-n-propylmethylamine; N,N-diisopropylmethylamine; N,N-di-n-butylmethylamine; N,N-di(2-methyl-n-propyl)methylamine; N,N-di(3-methyl-n-propyl)methylamine; N,N-di-n-propylethyalmine, N,N-diisopropylethylamine, N,N-di-n-butylethylamine, N,N-di(2-methyl-n-propyl)ethylamine; and N,N-di(3-methyl-n-propyl)ethylamine. Particularly desirable of these examples are triethylamine, N,N-di-n-propylethyalmine, N,N-diisopropylethylamine, N,N-di-n-butylethylamine, N,N-di(2-methyl-n-propyl)ethylamine, and N,N-di(3-methyl-n-propyl)ethylamine. Most desirable is N,N-diisopropylethylamine.

In the synthesis of O-alkylrapamycin derivatives by the process according to the present invention, the trialkylamine should be used in an amount not less than 5 mol, preferably not less than 10 mol, more preferably not less than 30 mol, per mol of rapamycin.

In the synthesis of O-alkylrapamycin derivatives by the process according to the present invention, the organic solvent is not specifically restricted so long as it dissolves the starting materials and the reaction products. It should preferably be a halogen-containing organic solvent, more preferably a chlorine-containing organic solvent, typically methylene chloride and chloroform.

In the synthesis of O-alkylrapamycin derivatives by the process according to the present invention, the organic solvent should be used in an amount not less than 1 part by weight, preferably 2 to 6 parts by weight, for 1 part by weight of rapamycin.

In the synthesis of O-alkylrapamycin derivatives by the process according to the present invention, the alkyl triflate should be used in an amount not less than 1 mol, preferably 5 to 20 mol, per mol of rapamycin.

The O-alkylrapamycin derivative synthesized by the process according to the present invention may be purified by dissolving the O-alkylrapamycin derivative in a water-miscible solvent such as alcohol and then placing the resulting solution in water for precipitation. Purification may also be accomplished by dissolving the O-alkylrapamycin derivative in a mixed solvent composed of water and at least one water-miscible solvent and allowing the resulting solution to stand for precipitation.

The purified O-alkylrapamycin derivative is powder. The powder has the advantage of improving the handling when coating to stent, the quality stability and the preservation stability.

The solvent used for purification of the O-alkylrapamycin synthesized by the process according to the present invention is not specifically restricted so long as it is miscible with water. It should preferably be an alcohol, particularly methanol.

For purification of the O-alkylrapamycin derivatives synthesized by the process according to the present invention, the solvent should be used in an amount not less than 3 parts by weight, preferably not less than 10 parts by weight, for 1 part by weight of O-rapamycin.

One use of the O-alkylrapamycin derivative synthesized by the process of the present invention is coating on a medical equipment, such as stent. The coated stent is indwelled in a lesion such as blood vessel, so that the O-alkylrapamycin derivative is uptaken into the lesion to prevent restenosis.

EXAMPLES

The invention will be described with reference to the following examples, which demonstrate the efficient production of O-alkylrapamycin derivatives by the process of the present invention.

Example 1

(1) Synthesis of 2-ethoxyethyl Triflate

In a round bottom flask containing a stirring bar was placed 9.0 g (100 mmol) of ethoxyethanol. The atmosphere in the flask was replaced with nitrogen by using a nitrogen bubbler. The flask was given 160 mL of methylene chloride and 23.3 mL (120 mmol) of 2,6-lutidine. The flask cooled with ice was given dropwise 20.2 mL (120 mmol) of trifluoromethanesulfonic acid anhydride over 20 minutes. After stirring for 1 hour, the reaction liquid was mixed with 20 mL of saturated solution of ammonium chloride. The resulting mixture was washed sequentially with 1N hydrochloric acid (100 mL), deionized water (100 mL), saturated solution of sodium hydrogen carbonate (100 mL), and saturated aqueous solution of sodium chloride (100 mL). The organic layer was separated and dried with anhydrous sodium sulfate. With the sodium sulfate filtered off, the solution was concentrated under reduced pressure. The residue underwent silica gel chromatography. Thus there was obtained 15.03 g (67.6% yields) of 2-ethoxyethyl triflate from the fraction in eluate of 20% ethyl acetate-hexane.

(2) Synthesis of 40-O-[(2'-ethoxy)ethyl]rapamycin

In a round bottom flask containing a stirring bar was placed 1.0 g (1.09 mmol) of rapamycin. With the flask connected to a condenser, the atmosphere in the flask was replaced with nitrogen by using a nitrogen bubbler. To the flask was added 3.5 mL of methylene chloride for dissolution. To the flask was further added 10 mL (57.5 mmol) of N,N-diisopropylethylamine and 1.95 g (8.78 mmol) of the previously synthesized 2-ethoxyethyl triflate with vigorous stirring. With the flask kept at 60° C. in an oil bath, the content was stirred for 1 hour and 20 minutes. The resulting mixture was diluted with 100 mL of ethyl acetate and washed sequentially with 100 mL of 1N hydrochloric acid, 100 mL of deionized water, and 80 mL of saturated aqueous solution of sodium chloride. The ethyl acetate phase was separated and then stirred with 5 g of anhydrous sodium sulfate for 20 minutes. With the sodium sulfate filtered off, the solution was concentrated by using a rotary evaporator. The concentrated solution was purified using a column chromatograph, with a silica gel bed measuring 4 cm in diameter and 26 cm high. Elution was accomplished by flowing sequentially 300 mL of ethyl acetate/n-hexane (1:1 v/v), 1000 mL of ethyl acetate/n-hexane (3:2, v/v), and 300 mL of ethyl acetate/n-hexane (7:3, v/v). The desired fraction was collected and concentrated, and the concentrate was vacuum dried in a desiccator. Thus there was obtained 494 mg (0.501 mmol) of the desired product (46% yields).

Example 2

In a round bottom flask containing a stirring bar was placed 1.0 g (1.09 mmol) of rapamycin. With the flask connected to a condenser, the atmosphere in the flask was replaced with nitrogen by using a nitrogen bubbler. To the flask was added 3.5 mL of chloroform for dissolution. To the flask was further added 10 mL (57.5 mmol) of N,N-diisopropylethylamine and 1.95 g (8.78 mmol) of the 2-ethoxyethyl triflate previously synthesized in Example 1 with vigorous stirring. With the flask kept at 60° C. in an oil bath, the content was stirred for 1 hour and 20 minutes. The resulting mixture was diluted with 100 mL of ethyl acetate and washed sequentially with 100 mL of 1N hydrochloric acid, 100 mL of deionized water, and 80 mL of saturated aqueous solution of sodium chloride. The ethyl acetate phase was separated and then stirred with 5 g of anhydrous sodium sulfate for 20 minutes. With the sodium sulfate filtered off, the solution was concentrated using a rotary evaporator. The concentrated solution was purified using column chromatograph, with a silica gel bed measuring 4 cm in diameter and 26 cm high. Elution was accomplished by flowing sequentially 300 mL of ethyl acetate/n-hexane (1:1, v/v), 1000 mL of ethyl acetate/n-hexane (3:2, v/v), and 300 mL of ethyl acetate/n-hexane (7:3, v/v). The desired fraction was collected and concentrated, and the concentrate was vacuum dried in a desiccator. Thus there was obtained 451 mg (0.458 mmol) of the desired product (42% yields).

Example 3

In a round bottom flask containing a stirring bar was placed 1.0 g (1.09 mmol) of rapamycin. With the flask connected to a condenser, the atmosphere in the flask was replaced with nitrogen by using a nitrogen bubbler. To the flask was added 3.5 mL of methylene chloride for dissolution. To the flask was further added 8 mL (57.4 mmol) of triethylamine and 1.95 g (8.78 mmol) of the 2-ethoxyethyl triflate previously synthesized in Example 1 with vigorous stirring. With the flask kept at 60° C. in an oil bath, the content was stirred for 1 hour and 20 minutes. The resulting mixture was diluted with 100 mL of ethyl acetate and washed sequentially with 100 mL of 1N hydrochloric acid, 100 mL of deionized water, and 80 mL of saturated aqueous solution of sodium chloride. The ethyl acetate phase was separated and then stirred with 5 g of anhydrous sodium sulfate for 20 minutes. With the sodium sulfate filtered off, the solution was concentrated using a rotary evaporator. The concentrated solution was purified using column chromatograph, with a silica-gel bed measuring 4 cm in diameter and 26 cm high. Elution was accomplished by flowing sequentially 300 mL of ethyl acetate/n-hexane (1:1, v/v), 1000 mL of ethyl acetate/n-hexane (3:2, v/v), and 300 mL of ethyl acetate/n-hexane (7:3, v/v). The desired fraction was collected and concentrated, and the concentrate was vacuum dried in a desiccator. Thus there was obtained 344 mg (0.349 mmol) of the desired product (32% yields).

Example 4

In 2 mL of methanol was dissolved 500 mg of the 40-O-[(2'-ethoxy)ethyl]rapamycin which had been obtained in Example 1. The resulting solution was added dropwise to 20 mL of deionized water with stirring. The solids which had precipitated out were filtered off and washed with a small amount of water and finally dried under reduced pressure at 40° C. for more than 10 hours. Thus there was obtained 483 mg of white powder.

This product gave an NMR chart as shown in FIG. 1. This NMR chart indicates the structure of 40-O-[(2'-ethoxy)ethyl]rapamycin represented by the general formula 4.

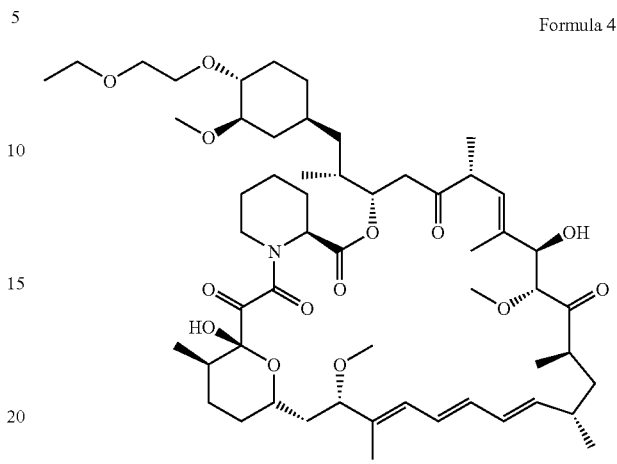

Formula 4

Comparative Example

A sample of 40-O-[(2'-ethoxy)ethyl]rapamycin was synthesized by the process disclosed in WO94/09010 official gazette so as to evaluate yields.

In a round bottom flask containing a stirring bar was placed 1.0 g (1.09 mmol) of rapamycin. With the flask connected to a condenser, the atmosphere in the flask was replaced with nitrogen by using a nitrogen bubbler. To the flask was added 3.5 mL of toluene for dissolution. To the flask was further added 467 mg (4.36 mmol) of 2,6-lutidine and 1.95 g (8.78 mmol) of the 2-ethoxyethyl triflate previously synthesized in Example 1 with vigorous stirring. With the flask kept at 60° C. in an oil bath, the content was stirred for 1 hour and 20 minutes. The resulting mixture was diluted with 100 mL of ethyl acetate and washed sequentially with 100 mL of 1N hydrochloric acid, 100 mL of deionized water, and 80 mL of saturated aqueous solution of sodium chloride. The ethyl acetate phase was separated and then stirred with 5 g of anhydrous sodium sulfate for 20 minutes. With the sodium sulfate filtered off, the solution was concentrated using a rotary evaporator. The concentrated solution was purified using column chromatograph, with a silica gel bed measuring 4 cm in diameter and 26 cm high. Elution was accomplished by flowing sequentially 300 mL of ethyl acetate/n-hexane (1:1, v/v), 1000 mL of ethyl acetate/n-hexane (3:2, v/v), and 300 mL of ethyl acetate/n-hexane (7:3, v/v). The desired fraction was collected and concentrated, and the concentrate was vacuum dried in a desiccator. Thus there was obtained 247 mg (0.251 mmol) of the desired product (23% yields).

What is claimed is:

1. A process for production of a compound represented by the formula (1) below by comprising conducting a reaction between rapamycin and alkyl triflate in an organic solvent which is a chlorine-containing organic solvent, wherein said reaction is carried out in the presence of trialkylamine, Formula 1

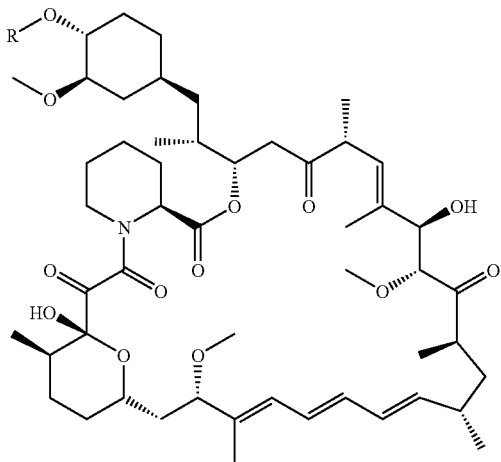

where R denotes alkyl, arylalkyl, hydroxyalkyl, alkoxyalkyl, acyloxyalkyl, aminoalkyl, alkylaminoalkyl, alkoxycarbonylaminoalkyl, acylaminoalkyl, or aryl.

2. The process as defined in claim 1, wherein the trialkylamine is used in an amount not less than 30 mol per mol of rapamycin.

3. The process as defined in claim 1, wherein the trialkylamine is N,N-diisopropylethylamine.

4. The process as defined in claim 1, wherein the chlorine-containing organic solvent is methylene chloride or chloroform.

5. The process as defined in claim 1, wherein the organic solvent is used in an amount of 2 to 6 parts by weight for 1 part by weight of rapamycin.

6. The process as defined in claim 1, wherein the alkyl triflate is used in an amount of 5 to 20 mol per mol of the compound represented by formula (1).

7. The process as defined in claim 1, wherein the alkyl triflate is 2-ethoxyethyl triflate.

8. The process as defined in claim 1, wherein said process includes an additional step for purification in which the compound represented by formula (1) is placed in a mixed solvent comprising water and at least one water-miscible solvent or placed in water or a water-containing mixed solvent after dissolution in at least one water-miscible solvent, and subsequently allowed to precipitate out.

9. The process as defined in claim 8, wherein the water-miscible solvent is used in an amount of 2 to 10 parts by weight for 1 part by weight of the compound represented by formula (1).

10. The process as defined in claim 8, wherein the water is used in an amount not less than 10 parts by weight for 1 part by weight of the compound represented by formula (1).

11. The process as defined in claim 8, wherein the water-miscible solvent is an alcohol.

12. The process as defined in claim 11, wherein the alcohol is methanol.

13. The process as defined in claim 8, wherein the step of precipitation is carried out such that the compound represented by formula (1) is dissolved in a solvent containing at least one water-miscible solvent and subsequently the resulting solution is placed in water or a mixed solvent comprising water and at least one water-miscible solvent.

* * * * *